(12) United States Patent
Psaros

(10) Patent No.: US 7,814,908 B2
(45) Date of Patent: Oct. 19, 2010

(54) METHOD AND DEVICE FOR REDUCING THE CARBON DIOXIDE CONTENT IN A DEAD VOLUME

(75) Inventor: Georgios Psaros, Tullinge (SE)

(73) Assignee: Maquet Critical Care AB, Solna (SE)

( * ) Notice: Subject to any disclaimer, the term of this patent is extended or adjusted under 35 U.S.C. 154(b) by 657 days.

(21) Appl. No.: 10/578,833

(22) PCT Filed: Nov. 8, 2004

(86) PCT No.: PCT/SE2004/001613

§ 371 (c)(1),
(2), (4) Date: May 10, 2006

(87) PCT Pub. No.: WO2005/049124

PCT Pub. Date: Jun. 2, 2005

(65) Prior Publication Data

US 2007/0062535 A1 Mar. 22, 2007

(30) Foreign Application Priority Data

Nov. 19, 2003 (SE) .................................... 0303064

(51) Int. Cl.
*A62B 23/02* (2006.01)

(52) U.S. Cl. .............................. 128/205.28; 128/205.12; 128/203.25

(58) Field of Classification Search ............ 128/204.18, 128/205.12, 204.22, 201.25, 203.25, 205.27, 128/205.28

See application file for complete search history.

(56) References Cited

U.S. PATENT DOCUMENTS

| 3,256,876 | A | * | 6/1966 | Elam ...................... | 128/205.15 |
| 4,127,121 | A | * | 11/1978 | Westenskow et al. ... | 128/203.14 |
| 5,400,778 | A | * | 3/1995 | Jonson et al. .......... | 128/205.19 |
| 5,673,688 | A | * | 10/1997 | Tham et al. ............ | 128/204.22 |
| 5,694,924 | A | * | 12/1997 | Cewers .................. | 128/204.21 |
| 5,806,513 | A | * | 9/1998 | Tham et al. ............ | 128/204.22 |
| 5,850,833 | A | * | 12/1998 | Kotliar .................. | 128/202.12 |
| 5,896,854 | A | * | 4/1999 | Bliss et al. ............. | 128/200.24 |
| 6,152,133 | A | * | 11/2000 | Psaros et al. ........... | 128/205.12 |
| 6,298,848 | B1 | * | 10/2001 | Skog ..................... | 128/204.18 |

FOREIGN PATENT DOCUMENTS

WO WO 91/19526 12/1991

OTHER PUBLICATIONS

L. Perhag, The Reflector: a new method for saving anaessthetic vapours, Apr. 11, 2000, Brithish Journal of Anaesthesia, vol. 95, p. 484-486.*

"Aspiration of Airway Dead Space: A New Method to Enhance $CO_2$ Elimination," De Robertis et al, American Journal of Respiratory and Critical Care Medicine, vol. 159, No. 3 (Mar. 1999), pp. 728-732.

* cited by examiner

*Primary Examiner*—Justine R Yu
*Assistant Examiner*—Christopher Blizzard
(74) *Attorney, Agent, or Firm*—Schiff Hardin LLP

(57) ABSTRACT

In a method and device for reducing the carbon dioxide content in a dead volume intended for connection to the respiratory system of a patient, and an anesthesia apparatus embodying such a device, a flow of gas is generated from an outlet associated with the dead volume and the gas is conducted through a carbon dioxide absorber, and the gas after passing through the carbon dioxide absorber is returned to an inlet associated with the dead volume.

7 Claims, 3 Drawing Sheets

METHOD AND DEVICE FOR REDUCING THE CARBON DIOXIDE CONTENT IN A DEAD VOLUME

BACKGROUND OF THE INVENTION

1. Field of the Invention

The present invention concerns a method for reducing a dead volume in an apparatus designed to be connected to the respiratory system of a patient.

The present invention is also directed to a device for reduction of dead volume in an apparatus designed to be connected to the respiratory system of a patient.

2. Description of the Prior Art

As a rule, when an apparatus is to be connected to the respiratory system of a patient, a machine dead volume is introduced. This dead volume results in carbon dioxide in expired gas from the patient being returned to the respiratory system with the following inspiration.

"Apparatus" as used herein relates to all respiratory apparatuses which can be connected to the respiratory system to condition respiratory gas, facilitate breathing, support breathing, control breathing, etc. Typical apparatuses of this type are respirators and ventilators for respiratory therapy treatment and anesthesia apparatuses.

"Patient" as used herein relates to all living creatures, but primarily humans and domesticated animals.

A known way to reduce reinspiration of gas mixed with carbon dioxide is described in WO 91/19526. According to the known method, gas is evacuated from the dead volume primarily during the final phase of expiration while fresh gas is concurrently provided.

A drawback with the known method is that limitations exist in the volume which can be evacuated. With the use of many components connected to the patient, for example, heat and moisture exchangers (HME), reflectors for anesthesia gas, bacteria filters, etc., the mechanical dead volume can be relatively large, 50-100 ml. This volume then approaches the same magnitude as the tidal volume—particularly if it is a child, small animal or adult with severe lung illness who is the patient.

Since the method according to WO 91/19526 is primarily directed to evacuating gas deep in the respiratory system of the patient it also requires very thin tubes. This results in significant low pressure being required to bring about a sufficient stream of evacuated gas. For obvious reasons a low pressure larger than about 1 atmosphere cannot be produced.

Therefore, a need for a method and a device for reducing a dead volume which has a broader applicability and which overcomes the problems named above exists.

SUMMARY OF THE INVENTION

An object of the present invention is to provide a method that at least partially solves the above-noted problems.

Another object of the present invention is to provide a device that at least partially solves the above-noted problems.

The object relating to the method is achieved in accordance with the present invention by a method including the steps of generating a flow of gas from an outlet associated with the dead volume, conducting the gas through an absorber for carbon dioxide, and returning the gas that has passed through the absorber to an inlet associated with the dead volume.

By suctioning a volume of gas out of the dead volume, removing carbon dioxide from that gas and then returning the cleaned gas to the dead volume, a simple and effective reduction of the carbon dioxide content is obtained in the mechanical dead volume. The gas can be suctioned out continually as well as intermittently.

In more advanced designs of the method, many steps can be executed on the gas sucked out of the dead volume. For example, the composition of the gas can be analyzed quantitatively and qualitatively. The composition of the gas can changed more than simply by removal of carbon dioxide. For example, by humidifying the gas, adding complementary or new gas components such as oxygen, anesthetic, medicament in gaseous form, etc.

The above object relating to the device is achieved in accordance with the present invention by a device having a flow generator that generates a flow of gas from an outlet associated with the dead volume to an inlet associated with the dead volume, and a carbon dioxide absorber that is connected in series with the flow generator for absorbing carbon dioxide out of the flow of gas.

By the use of a flow generator which generates a gas flow between an outlet associated with the dead volume and an inlet associated in series with the flow generator, a simple and effective device is obtained for reducing the carbon dioxide content in the mechanical dead volume.

In this connection, the absorber can be placed before as well as after the flow generator in the direction of gas flow.

In regard only to parts of the mechanical dead volume outside the patient, relatively coarse tubes can be used and the flow generator does not need to be designed to generate a vacuum or high pressure differences to generate a sufficient gas flow. The flow generator can be driven continually with a cancelled minute volume or work intermittently, synchronized with expirations or parts of expirations.

To reduce the risk of contamination, bacterial filters can be introduced in series with the flow generator and the absorber, between these and the outlet and inlet, respectively.

The outlet and the inlet can consist of adaptors designed to be coupled in series with the dead volume.

Further components can be coupled in series or parallel with the flow generator and the absorber.

The composition of the gas can be determined qualitatively and/or quantitatively with a gas monitor. This determination can be done before or after the carbon dioxide is absorbed (or both if two gas monitors or a parallel connected gas monitor is used).

With a gas conditioner the gas can be conditioned in a suitable way before it is returned to the dead volume. Conditioning can consist of humidifying the gas and/or complementing it with a gas component. A complementary gas component can be of oxygen, laughing gas, an anesthetic, a gaseous pharmaceutical, etc.

A particularly beneficial application of the device according to the invention is in an anesthesia apparatus. The design provides a compact, effective and safe anesthesia apparatus.

DESCRIPTION OF THE PREFERRED EMBODIMENTS

Figure 1:
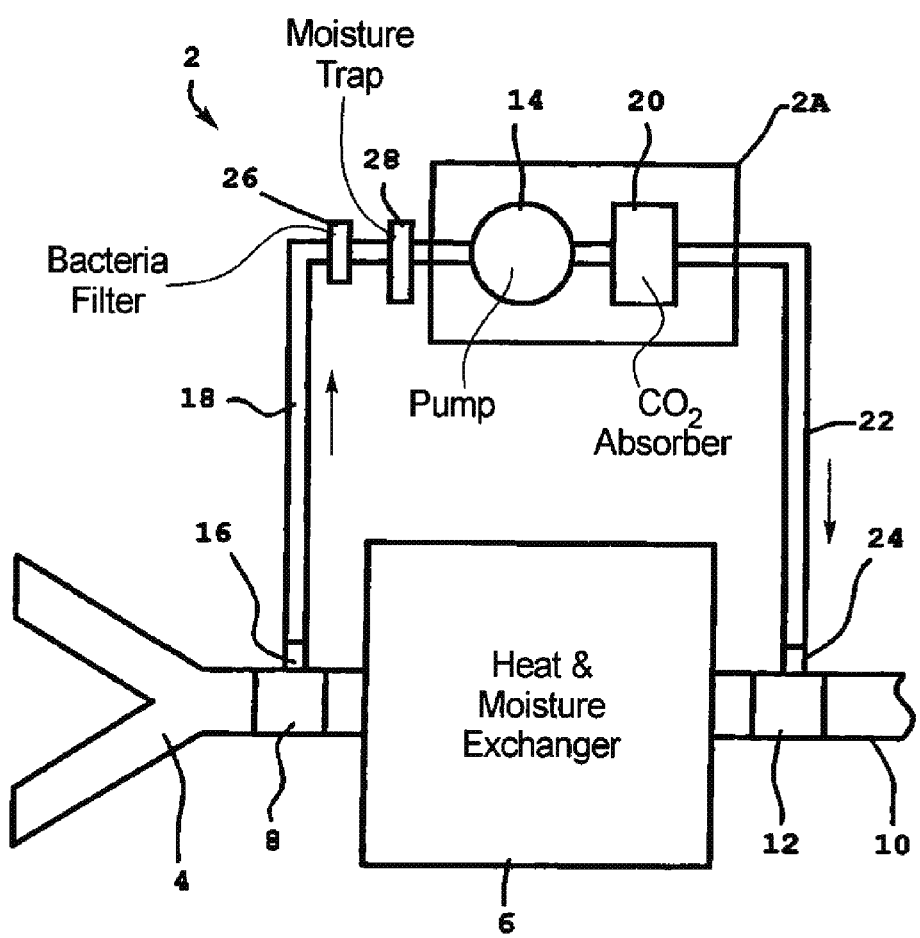
FIG. 1 is a schematic illustration of a first embodiment of a device according to the invention.

In FIG. 1 a first embodiment of a device 2 according to the invention is shown. The device 2 is coupled between a y-piece 4 via a first adapter 8 and a moisture and heat exchanger 6 and a patient connection 10 via a second adaptor 12.

The y-piece 4 is connected to a ventilator (not shown) or another conventional respiratory apparatus with separate flow passages for inspiration and expiration. Since such apparatuses are well known and the invention is not principally directed to functions or designs for them, they do not need to be described in this context.

It can be noted that the Y-piece 4 in this regard represents all known connections for respiratory apparatuses, for example coaxial connections such as Bain-system, etc.

The patient connection 10 can be any conventional patent connection, for example, tracheal tube, tracheotomy tube, tracheostomy tube, or a non-invasive face mask. These components are also well known and do not need to be described further in this context.

The moisture and heat exchanger 6 is a common component with respiratory therapy of different types. It absorbs moisture from gas during expiration and supplies moisture to gas during inspiration. A problem with the moisture and heat exchanger 6 is that it takes up a certain volume. This volume, together with the tube volume between the y-piece 4 up to and including the patient connection 10, form the machine dead volume. Gas mixed with carbon dioxide which is in this dead volume after expiration is returned to the patient during the following inspiration.

Since the machine dead volume can be relatively large in relation to the tidal volume which the patient inspires or is supplied during inspiration, the returned volume of carbon dioxide can result in disadvantages for the patient. The moisture and heat exchanger 6 alone can have a dead volume of 35-70 ml. With further components, for example bacteria filters in series with the moisture and heat exchanger 6, the dead volume can approach 100 ml. For an adult person with RDS (Respiratory Distress Symptom) or another lung disease, tidal volumes between 50 and 300 ml can be attainable without risking injury from the respiratory therapy (as compared to healthy lungs where 500 ml is a normal standard value for tidal volume).

To effectively reduce the carbon dioxide content in the machine dead volume, gas is suctioned from the dead volume by a pump 14 in the device. The pump 14 suctions the gas via an outlet 16 in the first adapter 8 and through a first tube 18 to a carbon dioxide absorber 20, arranged in series with the pump 14. After the carbon dioxide is absorbed by the absorber 20 the gas is returned to the dead volume via a second tube 22 and an inlet 24 in the second adapter 12.

The tubes 18, 22 as well as the adapters 8, 12 preferably are formed of disposable material, which is changed between each use. The absorbent material in the absorber 20 can be disposable or reusable.

In its simplest design a device according to the invention can be a stand alone unit formed by the pump 14 and the absorber 20, coupled in series with one another. In FIG. 1 such a stand alone unit has been indicated with a container 2A, within which these components are arranged. The container 2A can then in use be completed with necessary components to connect it to the dead volume.

Naturally, the device according to the invention can also be completely integrated in a respiratory apparatus.

It should be noted that the pump 14 herein can be any flow generating component, for example fan, turbine, piston pump, displacement pump, compressor, etc.

To reduce the need for advanced disinfecting between each use a bacteria filter 26 is preferably arranged between the pump 14 and the outlet 16. A bacteria filter can even be arranged between the absorber 20 and the input 24 (not shown) to completely separate container 2A from bacterial contamination.

Since the gas that is suctioned has a certain moisture content (moisture and heat exchanger 6 is not 100%), a water trap 28 can be arranged between the bacteria filter 26 and the pump 14.

The pump 14 preferably operates continuously and pumps a substantially constant volume of gas during both inspiration and expiration. With a pump speed of a few liters per minute an effective reduction of the carbon dioxide content in the dead volume can be obtained and also, consequently, a considerable reduction of reinspiration of carbon dioxide.

Naturally the pump 14 can operate intermittently, for example synchronous with the expirations (or a part of them). One advantage with continuous operation compared with intermittent is that the continuous operation is much simpler; there is no need for advanced control, no need for obtaining information on the breathing cycle (inspiration/expiration), etc.

The method and the device according to the invention result in many advantages. For example, components can be sized more effectively for their respective purposes, instead of for limiting the dead volume they contribute to the system.

More components can be placed in series between the Y-piece 4 and the patient connection 10 without affecting the reinspiration of carbon dioxide.

Particularly, the device 2 results in significant advantages with respiratory therapy in all patients with a very small tidal volume such as adults with serious lung illness, small children, infants, neonates and small animals. For these patient groups, it is necessary to continually consider which (dead volume candidates) components can be permitted without risking the tidal being to large.

The inlet 24 on the second adapter 12 and the outlet 16 on the first adapter 8, respectively, preferably is designed so that the gas simply flows out of or in to the dead volume, respectively. If a larger remixing of gas is desired at the inlet 24, this (or the second adapter 24) preferably is designed so that turbulent streams arise when the gas streams into the dead volume. Such turbulence can contribute to an increased mixing of the carbon dioxide blended gas in the patient connection 10.

It should be noted here that the pump 14 can also work in opposite direction, that is, to suck up gas from the second adapter 24, through the absorber 20, the pump 14 and back to the dead volume via the first adapter 8.

Consequently, it is possible to use the pump 14 intermittently for different directions, for example to drive the gas between the outlet 16 and the inlet 24 during the end of expiration and between the inlet 24 and the outlet 16 during the beginning of inspiration. This results in that the carbon dioxide content in the dead volume is diluted during expiration and then to at least a certain degree is removed from the dead volume during the beginning of inspiration. Other variants with inversion of the flow direction are possible and more preferably dependent upon the individual breathing pattern that exists for each patient.

It is noteworthy that the device does not need to contain separate adapters 8, 12. The y-piece 4, the moisture and heat exchanger 6 and the patient connection 10 instead can be provided with inlet 24 or outlet 16 which the tubes 22 and 18, respectively, can be connected to.

Figure 2:
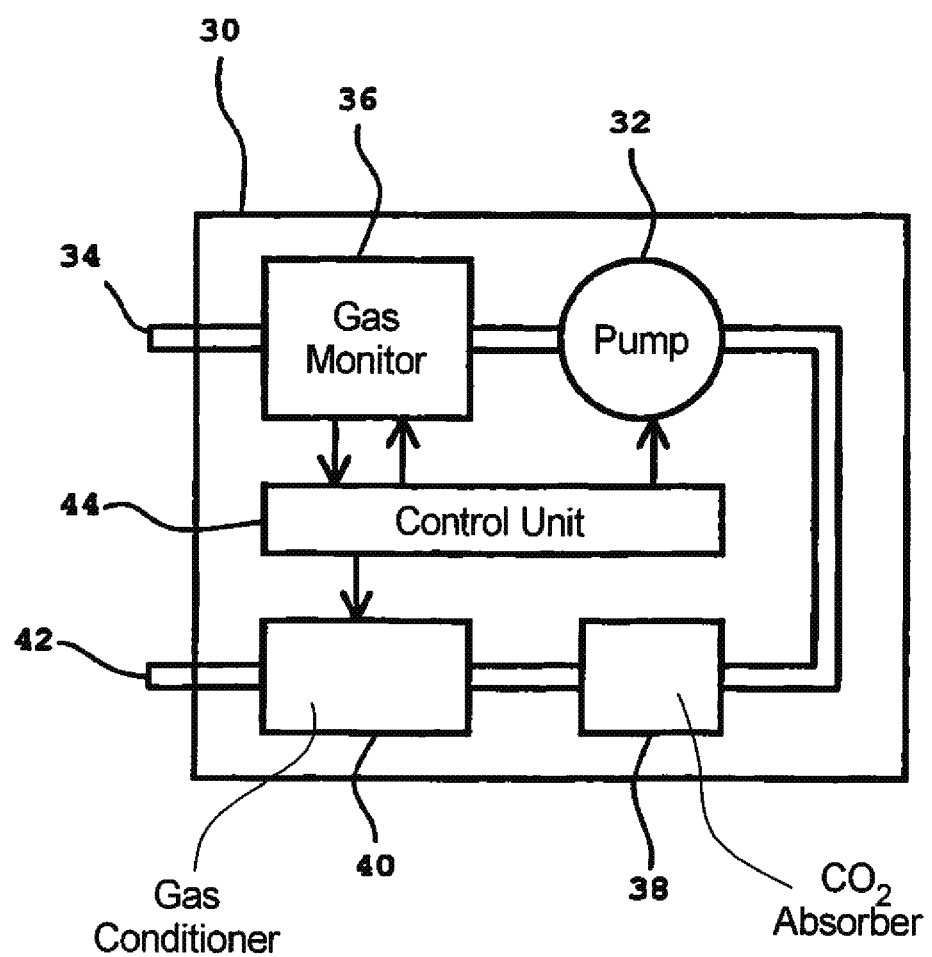
FIG. 2 is a schematic illustration of a second embodiment of a device according to the invention.

In FIG. 2 a second embodiment of a device 30 according to the invention is shown. The device 30 in this case consists of a pump 32 which sucks gas from a first connection 34, which is connectable to a dead volume (not shown). The device 30 further contains a gas monitor 36 for qualitative and/or quantitative analysis of the gas, a $CO_2$ absorber 38, a gas conditioner 40, a second connection 42 (connectable to the dead volume) and a control unit 44.

In the device 30 the gas that is suctioned out of the dead volume is analyzed. The analysis can be directed to one or many of the components in the gas, for example carbon dioxide, oxygen or a trace gas. The measured result is transferred to the control unit 44.

The control unit 44 can control the pump 14, the gas conditioner 40 and the gas monitor 36. By measuring the carbon dioxide content in the gas, the pump's 32 sucking effect can be regulated based on the carbon dioxide concentration, that is, essentially synchronized with expirations. The pump 32 can for example be synchronized between two suck effect levels, one for inspiration and one for expiration. Synchronization can even occur continuously, based directly upon the carbon dioxide content.

The control unit 44 can control the gas conditioner 40 to condition the gas which is restored. For example, by measuring the humidity in the gas monitor 36, the gas conditioner 40 can synchronize restoration of the humidity in the gas which is restored to the dead volume.

Alternatively, the oxygen percentage can be measured in the gas monitor 36 and oxygen supplied to the gas by the gas conditioner 40.

Further alternatives are that the percentage of gaseous medicament is measured in the gas monitor 36 and gaseous medicament is supplied to the gas in the gas conditioner 40.

The gas monitor 36 does not need to be placed upstream of the pump 32. It can be placed downstream of the absorber 38 or downstream of the gas conditioner 40. With the second placement the gas monitor 36 can be used for the second regulating, for example, feedback control of the above-named functions.

The gas monitor 36 can be substituted with a gas monitor which is connected in parallel to take a test sample from many positions in the flow path, for example, before and after the absorber 38, before and after the gas conditioner 40, etc.

Alternatively, multiple gas monitors can be arranged in different places in the device 40.

Figure 3:
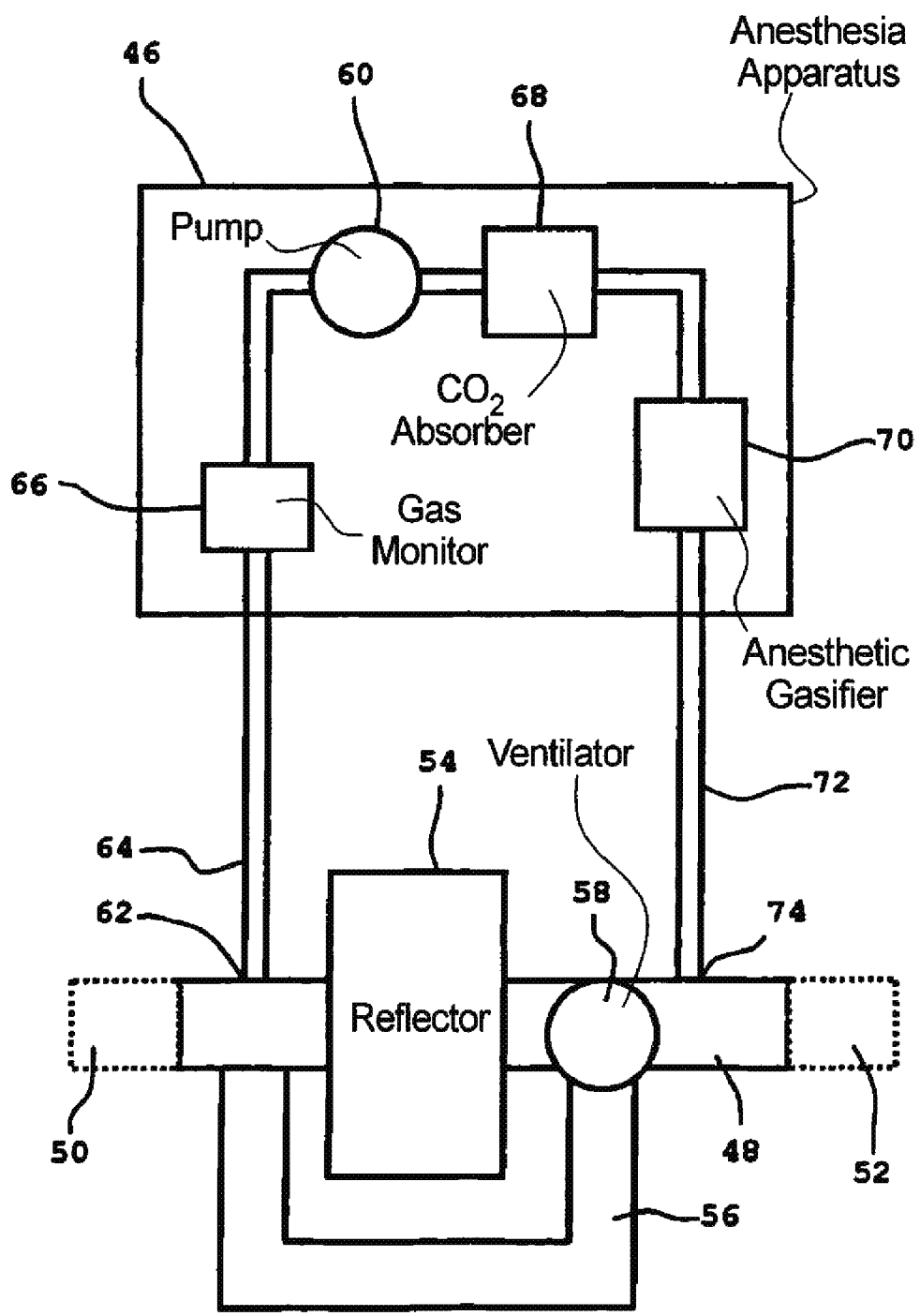
FIG. 3 illustrates an embodiment of an anesthesia apparatus having a device according to the invention embodied therein.

In FIG. 3 an embodiment of an anesthesia apparatus 46 that functions according to the same principles as the device according to the invention is shown.

The anesthesia apparatus 46 contains a gas line 48 which can be connected to a conventional ventilator or another breathing apparatus that is indicated with the dashed first connection part 50 and to a patient which is indicated with the dashed second connection part 52. The first connection part 50 may be a Y-piece 4 according to FIG. 1 or another component that is connected to a ventilator or breathing apparatus. The second coupling part 52 can be the patient connection 12 or the moisture and heat exchanger 6 according to FIG. 1 or some other component which leads to the patient.

A reflector 54 is arranged in the gas line 48. The reflector is a component which adsorbs anesthetic during expiration and resorbs the anesthetic during inspiration. This component is known from for example, EP 359755.

To be able to quickly stop the supply of anesthetic to the patient, the anesthesia apparatus 46 is provided with a bypass line 56, which leads the gas past the reflector 54. A ventilator 58 can be used to direct which flow route the gas shall follow, via the reflector 54 or via the bypass line 56.

It should be noted that the reflector 54 can be combined with a moisture and heat exchanger (not shown) either as a serial coupled physical component (possibly in the same cover as the reflector 54) or functionally by choosing a material for the reflector 54 which possibly adsorbs and resorbs even humidity and heat (in addition to the anesthetic).

To effectively minimize the reinspiration of carbon dioxide which collects in the mechanical dead volume consisting of the reflector 54 and the lines 48, a pump 60 is arranged to suck gas from the dead volume via an outlet 62. The suctioned gas passes a first tube 64, a gas monitor 66, an absorber for carbon dioxide 68, a gasifier for anesthetic 70 and a second tube 72 before it is returned to the dead volume via an inlet 74.

The gas that is suctioned out in this connection has effectively been cleaned of carbon dioxide simultaneously as it has been enriched with a suitable dose of anesthetic (depending on the measured concentration via the gas monitor 68).

The anesthesia apparatus 46 can be designed in many different ways without changing the underlying principles of reduction of reinspired carbon dioxide via use of a reflector 54.

In principle, it is sufficient to only use the pump 60 and the absorber 68 to reduce the carbon dioxide content. Conditioning of the gas with anesthetic can occur in another way, with dosing of anesthetic in gaseous form to the reflector 54 or the tube 48 or in liquid form to a gasifying body (not shown) in the reflector 54 or the line 48. The anesthetic can even be supplied directly to the second coupling part 52 or to the patient connection.

Determination of the gas concentrations can occur by conventional measurements through sucking out gas from the line 48 or another place. A measurement sensor can be placed in direct contact with the gas which flows in the tube 48, or in another place in the system.

The three embodiments in FIGS. 1, 2 and 3 can be combined in different ways. The basis of the invention is that, by means of only a few components, a flow generator and an absorber for carbon dioxide, it is possible to have an effective method for reducing the carbon dioxide content in a dead volume, so that reinspiration of carbon dioxide can be essentially reduced.

Although modifications and changes may be suggested by those skilled in the art, it is the invention of the inventor to embody within the patent warranted heron all changes and modifications as reasonably and properly come within the scope of his contribution to the art.

I claim as my invention:

1. A method for reducing the carbon dioxide content in a dead volume in a breathing apparatus, comprising the steps of:

respirating a patient with a gas supplied to the patient via a primary gas flow path containing a dead space into which carbon dioxide containing gas is exhaled by the patient that is re-breathed by the patient in a subsequent inhalation by the patient, said dead space having opposite first and second sides with said first side being closer to the patient than said second side;

connecting a bypass path at respective bypass connections at said opposite sides of said dead space and generating a gas flow of said exhaled gas from said dead space through said bypass path from said second side to said first side and through a carbon dioxide absorber in said bypass path; and returning gas that has passed through the carbon dioxide absorber from the bypass path to said primary gas flow path at said first side of said dead space, with said gas that passed through said dead volume and said carbon dioxide absorber then being inhaled by said patient.

2. Method according to claim 1, comprising continuously generating the gas flow.

3. Method according to claim 1 comprising conducting the gas flow past a gas monitor for at least one of qualitative and qualitative determination of a partial component in the gas.

4. An anesthesia apparatus comprising:

a primary gas flow path having a first end configured for gaseous connection to a ventilator and a second end configured to communicate with the respiratory system of a patient to be artificially respirated by said ventilator with gas containing an anesthetic, said primary gas flow path having a dead space therein in which carbon dioxide-containing gas exhaled by the patient is located that is re-breathed by the patient in a subsequent inhalation by the patient, said dead space having opposite first and second sides with said first side being closer to the patient than said second side;

a reflector located in said dead space of said primary gas flow path between said first side of said dead space and said second side of said dead space, that absorbs and desorbs said anesthetic;

a bypass outlet from said primary gas flow path located between said first end and said second side of said dead space, and a bypass inlet to said first gas flow path located between said second end and said first side of said dead space;

a bypass flow path connected between said bypass outlet and said bypass inlet, that bypasses said dead space;

a carbon dioxide absorber connected in said bypass flow path;

a flow generator connected in said bypass flow path in series with said carbon dioxide absorber that conducts said gas from said bypass outlet through said carbon dioxide absorber to remove carbon dioxide from the exhaled gas in the dead space and returns gas after passing through said carbon dioxide absorber to said primary gas flow path via said bypass inlet for inhalation by said patient via said second end.

5. An anesthesia apparatus according to claim 4, comprising a gas monitor connected in series with the flow generator and the absorber for at least one of qualitative and quantitative determination of a partial component in the gas.

6. An anesthesia apparatus according to claim 4 comprising a gas conditioner connected in series with the flow generator and the absorber for conditioning of the flowing gas.

7. An anesthesia apparatus according to claim 6 wherein the gas conditioner is a gasifier for liquid anesthetic.

* * * * *